(12) United States Patent
Kim et al.

(10) Patent No.: US 9,656,072 B2
(45) Date of Patent: May 23, 2017

(54) COCHLEAR IMPLANT APPARATUS FOR ACTIVE FEEDBACK CONTROL AND ACTIVE FEEDBACK CONTROL METHOD FOR THE SAME

(71) Applicants: KOREA INSTITUTE OF MACHINERY & MATERIALS, Daejeon (KR); INDUSTRIAL COOPERATION FOUNDATION OF CHONBUK NATIONAL UNIVERSITY, Jeonju-si (KR)

(72) Inventors: Wan-Doo Kim, Daejeon (KR); Shin Hur, Daejeon (KR); Young Do Jung, Seoul (KR); Yoon-Bong Hahn, Jeonju-si (KR); Yong-Kyu Park, Jeonju-si (KR); Seung Ha Oh, Seoul (KR); Juyong Chung, Yongin-si (KR); Sung June Kim, Seoul (KR); Yoon-Kyu Song, Yongin-si (KR); Won Hee Lee, Anyang-si (KR)

(73) Assignees: KOREA INSTITUTE OF MACHINERY & MATERIALS, Daejeon (KR); INDUSTRIAL COOPERATION FOUNDATION OF CHONBUK NATIONAL UNIVERSITY, Jeonju-si (KR)

( * ) Notice: Subject to any disclaimer, the term of this patent is extended or adjusted under 35 U.S.C. 154(b) by 92 days.

(21) Appl. No.: 14/377,617

(22) PCT Filed: Feb. 12, 2013

(86) PCT No.: PCT/KR2013/001073
§ 371 (c)(1),
(2) Date: Aug. 8, 2014

(87) PCT Pub. No.: WO2013/119093
PCT Pub. Date: Aug. 15, 2013

(65) Prior Publication Data
US 2016/0015973 A1    Jan. 21, 2016

(30) Foreign Application Priority Data

Feb. 10, 2012  (KR) .................. 10-2012-0013980

(51) Int. Cl.
*A61N 1/00* (2006.01)
*A61N 1/36* (2006.01)
(Continued)

(52) U.S. Cl.
CPC ....... *A61N 1/36032* (2013.01); *A61N 1/0541* (2013.01); *H04R 17/02* (2013.01);
(Continued)

(58) Field of Classification Search
CPC .......................... A61N 1/36032; A61N 1/0541
(Continued)

(56) References Cited

U.S. PATENT DOCUMENTS 8,073,547 B2    12/2011  Hong
8,165,688 B2    4/2012   Hur
(Continued)

FOREIGN PATENT DOCUMENTS

JP    10-056679      2/1998
JP    2004-081295    3/2004
(Continued)

*Primary Examiner* — Nadia A Mahmood
(74) *Attorney, Agent, or Firm* — Lex IP Meister, PLLC

(57) ABSTRACT

The present invention relates to a cochlear implant apparatus, and more particularly, to a cochlear implant apparatus capable of controlling the sensitivity or selectivity of sound through actuators. In accordance with an exemplary embodiment of the present invention, a cochlear implant apparatus for active feedback control which is inserted into the human body and configured to detect a sound in each frequency (Continued)

band includes a sensor unit configured to detect vibration according to a sound and generate an electrical signal corresponding to a magnitude of the vibration and actuators disposed in the sensor unit and each configured to react to the electrical signal and to control sensitivity according to the magnitude of the sound or the selectivity of a sound detected in each frequency band.

13 Claims, 14 Drawing Sheets

(51) Int. Cl.
    *A61N 1/05*     (2006.01)
    *H04R 17/02*     (2006.01)
    *H04R 31/00*     (2006.01)
    *H04R 1/08*     (2006.01)

(52) U.S. Cl.
    CPC ........... *H04R 31/006* (2013.01); *H04R 1/083* (2013.01); *H04R 2430/03* (2013.01)

(58) Field of Classification Search
    USPC ........................................................ 607/57, 7
    See application file for complete search history.

(56) References Cited

U.S. PATENT DOCUMENTS

2005/0234548 A1* 10/2005 Yuasa ................ A61N 1/36032
    623/10
2009/0112288 A1* 4/2009 Hur ........................ H04R 25/70
    607/57

FOREIGN PATENT DOCUMENTS

| KR | 10-2005-0008067 | 1/2005 |
| KR | 10-2009-0041892 | 4/2009 |
| KR | 10-2009-0041893 | 4/2009 |

\* cited by examiner

COCHLEAR IMPLANT APPARATUS FOR ACTIVE FEEDBACK CONTROL AND ACTIVE FEEDBACK CONTROL METHOD FOR THE SAME

CROSS-REFERENCE TO RELATED APPLICATION

This application claims priority to and the benefit of Korean Patent Application No. 10-2012-0013980 filed in the Korean Intellectual Property Office on Feb. 10, 2012, published as Korean Patent Publication No. 10-2013-0092318, now Korean Patent No. 10-1346710, the entire contents of which are incorporated herein by reference.

TECHNICAL FIELD

The present invention relates to a cochlear implant apparatus, and more particularly, to a cochlear implant apparatus capable of controlling the sensitivity or selectivity of sound through actuators.

BACKGROUND ART

Many medical devices for helping people who have lost their hearing by nature or in the course of their lifetime are being developed. In particular, a cochlear implant apparatus that helps people having live auditory nerves to sense sound by stimulating the auditory nerves with electricity has been recognized as being the most efficient device of tributary nerve devices that have now been developed so far. The transplant operations of such cochlear implant apparatuses are increased every year.

The conventional cochlear implant apparatus may be divided into a part outside the body and a part inside the body depending on its installation place. The conventional cochlear implant apparatus is configured to include an external device configured to receive sound outside the human body and an internal device inserted into the human body and configured to stimulate the auditory nerves. The part outside the body that is installed outside the body includes a microphone (or a transmitter), a sound processor (or a language synthesizer), and an antenna for transmission (or a sender). In this case, the microphone and the antenna for transmission are also called a headset. The part inside the body that is implanted into the body includes an receptor/stimulator (or a receiver) and an electrode.

Accordingly, in the conventional cochlear implant apparatus, a sound signal transferred by the microphone attached outside the human body is subject to the amplification of an external sound processor and the filtering of a filter without passing through an ark shell or the auditory ossicles. Physical vibration obtained by such processes is converted into an electrical signal and is transferred to the auditory ganglion through the electrode implanted within the cochlear implant apparatus. To this end, the conventional cochlear implant apparatus requires the transmitter configured to receive sound outside the body and an external device that consumes a lot of power in order to analyze and process the sound signal and to convert the processed signal into an electrical signal.

Accordingly, the conventional cochlear implant apparatus is problematic in that a long time is taken for a user to be accustomed to the cochlear implant apparatus as part of his body because separate equipment must be always attached outside the human body and a third party may become aware of the cochlear implant apparatus.

Furthermore, pieces of sound present in the natural world have a severe pressure deviation. A difference between small sound and great sound is about 180 dB, that is, a difference corresponding to trillions. A microphone capable of linearly processing such sound pressure is now not present. A device capable of processing such sound process most efficiently may be said to be a cochlea within the body.

In this case, the cochlea of the human body includes an outer hair cell and an inner hair cell. The outer hair cell becomes long in a low frequency and becomes short in a high frequency. The cochlea can recognize sounds of various magnitudes according to a pressure deviation through a change in the length of the hair cells. That is, the outer hair cell of the cochlea changes its length depending on sound pressure so that an excessively great sound is recognized as being small and an excessively small sound is recognized as being great.

The conventional cochlear technology, however, does not implement a mechanism, such as the outer hair cell of the cochlea, and is problematic in that sound of various magnitudes are not classified and recognized because a change according to a pressure deviation between the sounds is not detected.

For this reason, recently, there is a need for a technology capable of dividing sounds of various magnitudes according to a pressure deviation and controlling the sensitivity of a sound by simulating a mechanism, such as the outer hair cell of the cochlea.

RELATED ART DOCUMENT

Patent Document

[Korean Patent No. 10-0932204]

The related art relates to the frequency analyzer of an MEMS structure cochlear implant having a self-power function, wherein an upper structure is stacked on a lower structure. The upper structure includes a first substrate and a nanopillar contact portion formed over the first substrate, configured to have a lower part having a sawtooth form, and coated with platinum. The lower structure includes a second substrate configured to have a predetermined space unit for receiving a fluid formed therein and to have part of an upper part thereof opened, a base film formed over the fluid within the space unit of the second substrate, a plurality of consecutive first electrodes formed on the base film and configured to have a different interval between the first electrodes, that is, the width "w" of the first electrode and the length L of the first electrode, so that a received sound wave can be better transferred, nanopillars grown on the first electrodes in a specific direction and configured to have piezoelectric and semiconductor characteristics, and a sound wave inlet, that is, a passage configured to have a sound wave move the fluid within the space unit of the lower structure when the sound wave is generated. In such a structure, when the upper structure is stacked on the lower structure, the nanopillars of the lower structure are brought in contact with the nanopillar contact portion of the upper structure. When a sound wave is generated, the sound wave moves the fluid within the lower structure. Accordingly, a specific location of the base film is moved in a specific frequency component of the sound wave, the nanopillars brought in contact with the first electrodes on the base film are deformed, the deformed nanopillars come in contact with the nanopillar contact portion of the upper structure, and thus the nanopillars fixed to the short first electrodes and the nanopillars fixed to the long first electrodes generate electrical signals (current) of specific frequencies corresponding to a high frequency component and a low frequency component.

DISCLOSURE

Technical Problem

The present invention has been made in an effort to provide a cochlear implant apparatus and method having an advantage of controlling the sensitivity or selectivity of sound through actuators.

Accordingly, a recent cochlear implant apparatus requires a technology for inserting external devices exposed outside the human body into the human body and controlling the sensitivity of sound.

Technical Solution

An exemplary embodiment of the present invention provides a cochlear implant apparatus for active feedback control, which is capable of dividing and recognizing sounds of various magnitudes according to a pressure deviation by simulating the mechanism of the outer hair cell of the cochlea through actuators driven in response to the sound pressure of a sound.

Another embodiment of the present invention provides a cochlear implant apparatus for active feedback control, which is capable of controlling sensitivity in each frequency band through a plurality of actuators included in respective channels.

Yet another embodiment of the present invention provides a cochlear implant apparatus for active feedback control, which is capable of more effectively controlling the sensitivity of a sound using actuators suitable for the type of sensor.

In accordance with an exemplary embodiment of the present invention, there is provided a cochlear implant apparatus for active feedback control which is inserted into the human body and configured to detect a sound in each frequency band, including a sensor unit configured to detect vibration according to a sound and generate an electrical signal corresponding to the magnitude of the vibration and actuators disposed in the sensor unit and each configured to react to the electrical signal and to control sensitivity according to the magnitude of the sound or the selectivity of a sound detected in each frequency band.

Furthermore, the cochlear implant apparatus further includes an amplification unit configured to amplify the electrical signal from the sensor unit and provide the amplified electrical signal to the actuator and a control unit configured to process the amplified electrical signal received from the amplification unit and to provide the processed electrical signal to the amplification unit or the actuator.

Furthermore, the sensor unit includes nanopillars or piezoelectric elements.

In accordance with a first exemplary embodiment of the present invention, there is provided a cochlear implant apparatus for active feedback control, including a sensor unit, wherein the sensor unit includes a first substrate, a second substrate disposed to face the first substrate, and a plurality of base units disposed between the first substrate and the second substrate and configured to have different frequency bands and detects a sound in each frequency band through nanopillars formed in each of the plurality of base units, and the sensor unit includes actuators disposed between the first substrate and the second substrate and configured to support the first substrate and the second substrate or to move up and down in response to an electrical signal.

Furthermore, the actuators in accordance with an exemplary embodiment of the present invention are disposed on both sides of the base units and are consecutively connected along the first substrate or the second substrate.

Furthermore, the electrical signal has been converted based on the magnitude of vibration corresponding to a sound detected by the sensor unit.

Furthermore, the actuators are disposed in the respective base units and spaced apart from each other.

Furthermore, each of the actuators disposed in the respective base units moves up and down in response to an electrical signal corresponding to a sound detected from each of the base units.

In accordance with a second exemplary embodiment of the present invention, there is provided a cochlear implant apparatus for active feedback control, including a sensor unit configured to detect a sound through a frequency separation unit comprising a first electrode, a second electrode disposed to face the first electrode, and piezoelectric layer made of piezoelectric material and interposed between the first electrode and the second electrode, separating a sound according to each frequency band and generating an electrical signal, and the sensor unit includes an actuator configured to respond to the electrical signal and move the frequency separation unit.

Furthermore, the frequency separation unit in accordance with an exemplary embodiment of the present invention is divided into a plurality of frequency separation units in order to detect a sound according to each frequency band, and the actuator is disposed in each of the plurality of frequency separation units.

Furthermore, the actuator is disposed under the frequency separation unit.

In accordance with an exemplary embodiment of the present invention, there is provided an active feedback control method of a cochlear implant apparatus, including detecting, by a sensor unit, a sound within a human body, converting the detected sound into an electrical signal according to the magnitude of the detected sound, and outputting the converted electrical signal; amplifying, by an amplification unit, the electrical signal received from the sensor unit; and receiving, by an actuator, the amplified electrical signal from the amplifier and controlling a sensitivity of the sound detected by the sensor unit or the selectivity of the sound in each frequency band in response to the electrical signal.

Furthermore, the sensor unit includes nanopillars or piezoelectric elements.

Advantageous Effects

As described above, an exemplary embodiment of the present invention provides a cochlear implant apparatus for active feedback control, which is capable of dividing and recognizing sounds of various magnitudes according to a pressure deviation by simulating the mechanism of the outer hair cell of the cochlea through actuators driven in response to the sound pressure of a sound.

Furthermore, an exemplary embodiment of the present invention provides a cochlear implant apparatus for active feedback control, which is capable of controlling sensitivity in each frequency band through a plurality of actuators included in respective channels.

Furthermore, an exemplary embodiment of the present invention provides a cochlear implant apparatus for active feedback control, which is capable of more effectively controlling the sensitivity of a sound using actuators suitable for the type of sensor.

MODE FOR INVENTION

Figure 1:
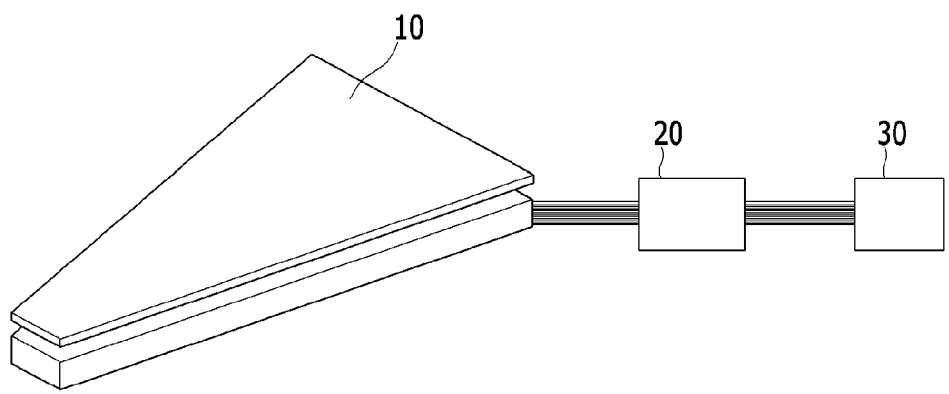
FIG. 1 is a schematic diagram illustrating a schematic configuration of a cochlear implant apparatus for active feedback control in accordance with an exemplary embodiment of the present invention.

Exemplary embodiments of the present invention may be modified in various forms, and the scope of the present invention should not be interpreted as being limited to the following exemplary embodiments. The exemplary embodiments of the present invention are intended to fully describe the present invention to those skilled in the art. Accordingly, the shapes, etc., of elements in the drawings may have been enlarged in order to highlight a more full description.

Hereinafter, some exemplary embodiments of the present invention are described in detail with reference to FIGS. 1 to 14.

FIG. 1 is a schematic diagram illustrating a schematic configuration of a cochlear implant apparatus for active feedback control in accordance with an exemplary embodiment of the present invention.

The cochlear implant apparatus for active feedback control of FIG. 1 according to an exemplary embodiment of in accordance with an exemplary embodiment of the present invention includes a sensor unit 10, an amplification unit 20, and a control unit 30.

The sensor unit 10 detects vibration according to a sound and generates an electrical signal corresponding to the magnitude of the detected vibration. Furthermore, the sensor unit 10 may divide the sound for each frequency band and generate the electrical signal. Furthermore, the frequency band may be implemented in 16 to 20 channels.

The amplification unit 20 receives the electrical signal from the sensor unit 10 and amplifies the received electrical signal in a specific size. Furthermore, the amplification unit 20 sends the amplified electrical signal to the control unit 30 to be described later. Furthermore, the amplification unit 20 may directly provide the amplified electrical signal to actuators to be described later.

The control unit 30 functions to convert the amplified electrical signal from the amplification unit 20 into a proper form through a task, such as a task for removing noise, decode basic parameters, store the decoded parameters, and generate current to be provided to an electrode unit (not illustrated) from the amplified electrical signal.

Furthermore, the control unit 30 processes the amplified electrical signal received from the amplification unit 20. In this case, the control unit 30 may provide the processed electrical signal to the actuators via the amplification unit 20 or may directly provide the processed electrical signal to the actuators.

Figure 2:
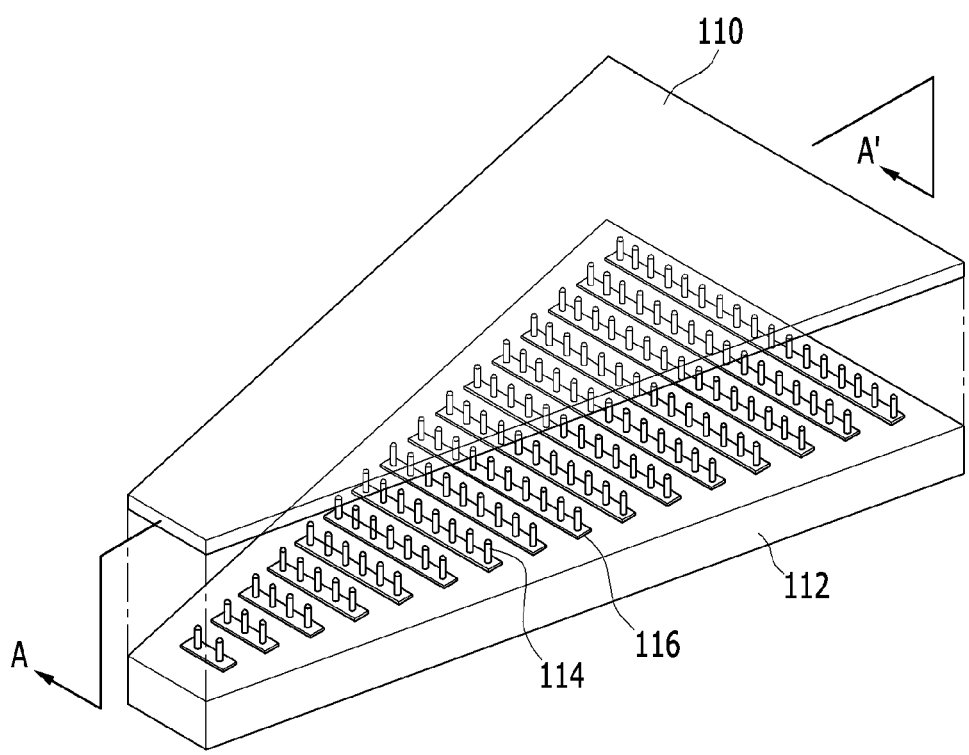
FIG. 2 is a perspective view of a sensor unit of the cochlear implant apparatus for active feedback control including nanopillars in accordance with an exemplary embodiment of the present invention.
Figure 3:
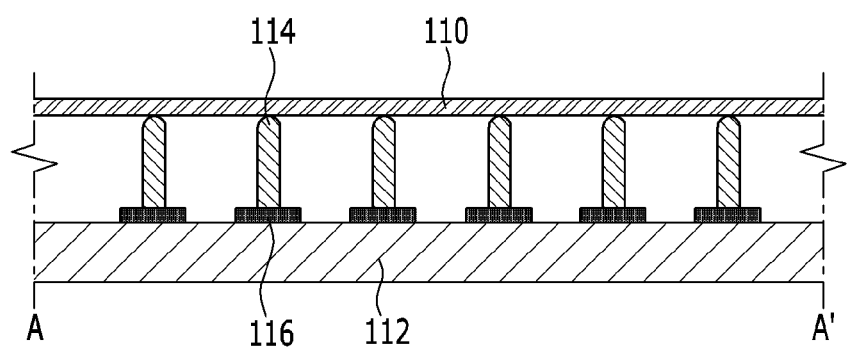
FIG. 3 is a cross-sectional view of the sensor unit taken along line A-A' of FIG. 2.

FIG. 2 is a perspective view of a sensor unit 100 of the cochlear implant apparatus for active feedback control including nanopillars 114, and FIG. 3 is a cross-sectional view of the sensor unit 100 taken along line A-A' of FIG. 2.

Referring to FIGS. 2 and 3, the sensor unit 100 of the cochlear implant apparatus for active feedback control including the nanopillars 114 in accordance with an exemplary embodiment of the present invention includes a first substrate 110, a second substrate 112, the nanopillars 114, and base units 116.

The first substrate 110 is symmetrical to the second substrate 112 and disposed to face the second substrate 112. The nanopillars 114 and the base units 116 are disposed between the first substrate 110 and the second substrate 112. In this case, the first substrate 110 is formed of a silicon wafer having a flat panel shape.

The second substrate 112 is a member combined with the first substrate 110 and configured to determine an outward appearance of the sensor unit 100. The second substrate 112 is made of silicon (Si) materials. Furthermore, a reception space configured to receive a propagation medium (not illustrated) and to have a specific shape may be formed in the second substrate 112.

Each of the nanopillars 114 has a nanopillar form, and a plurality of the nanopillars 114 is disposed in each of the base units 116. Furthermore, the nanopillar 114 is deformed in response to a movement of the base unit 116 that is deformed in response to the vibration of a sound and that will be described later. In this case, such a modification generates an electrical signal corresponding to the magnitude of the sound.

The base units 116 are disposed on the second substrate 112. A plurality of the base units 116 is divided according to each frequency band and detects frequencies in different regions. Furthermore, as described above, the base unit 116 is moved according to each frequency region depending on the vibration of a sound. Such a movement is delivered to the nanopillars 114.

Figure 4:
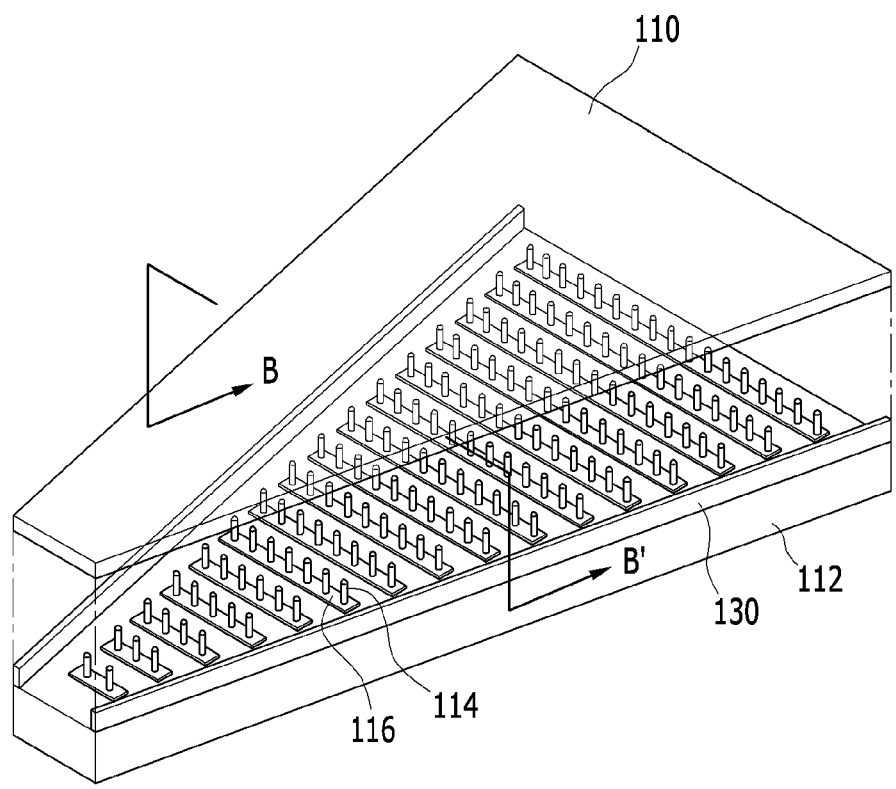
FIG. 4 is a perspective view illustrating a sensor unit of the cochlear implant apparatus for active feedback control in accordance with a first exemplary embodiment of the present invention.
Figure 5:
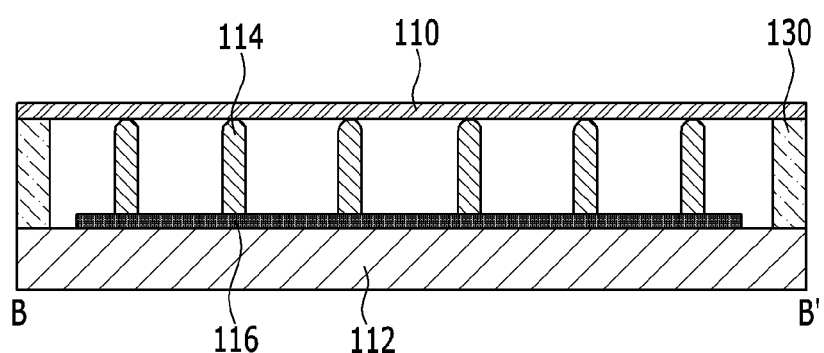
FIG. 5 is a cross-sectional view of the sensor unit taken along line B-B' of FIG. 4.

FIG. 4 is a perspective view illustrating a sensor unit 100 of the cochlear implant apparatus for active feedback control in accordance with a first exemplary embodiment of the present invention, and FIG. 5 is a cross-sectional view of the sensor unit 100 taken along line B-B' of FIG. 4.

Referring to FIGS. 4 and 5, the sensor unit 100 of the cochlear implant apparatus for active feedback control in accordance with a first exemplary embodiment of the present invention further includes an actuator 130.

The actuator 130 is disposed in the sensor unit 100 and is configured to react to an electrical signal and to control sensitivity according to the magnitude of a sound.

Such actuators 130 are disposed on both sides of the base units 116 and may be consecutively connected along the first substrate 110 or the second substrate 112.

Accordingly, the actuators 130 in accordance with the first exemplary embodiment of the present invention are disposed between the first substrate 110 and the second substrate 112 and are configured to support the first substrate 110 and the second substrate 112 or to move up and down in response to an electrical signal.

Figure 6:
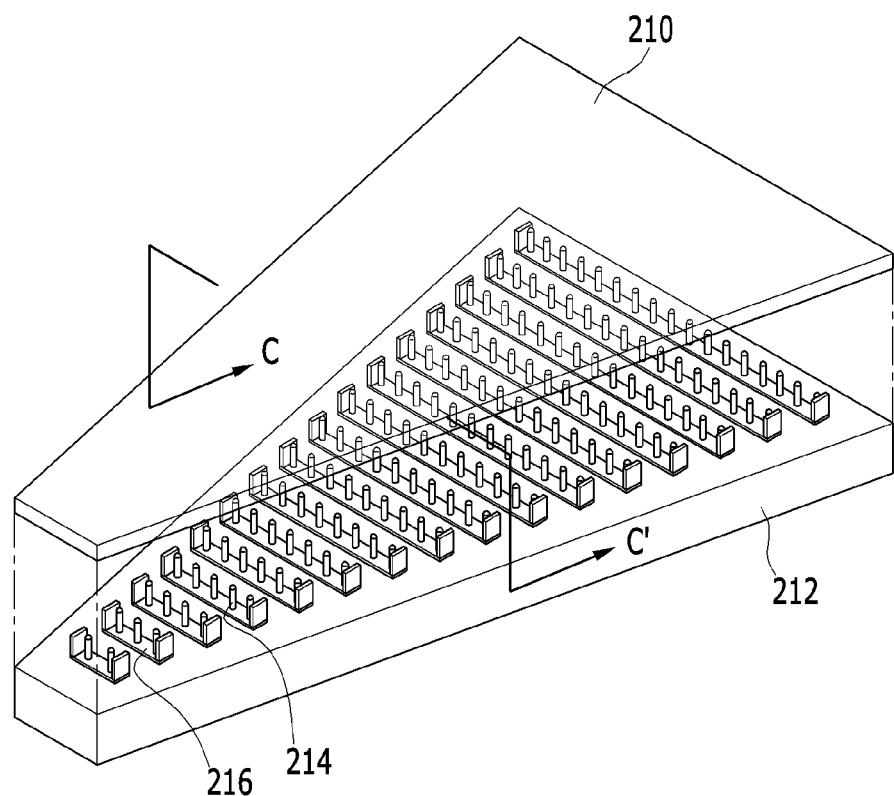
FIG. 6 is a perspective view illustrating a sensor unit of the cochlear implant apparatus for active feedback control in accordance with a second exemplary embodiment of the present invention.
Figure 7:
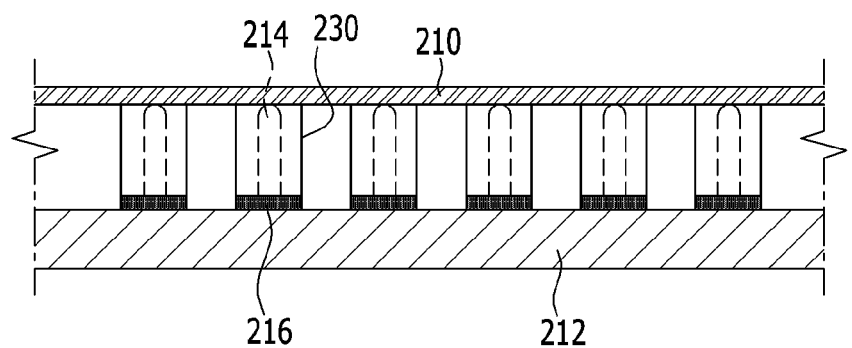
FIG. 7 is a side view illustrating one side of the sensor unit illustrated in FIG. 6.
Figure 8:
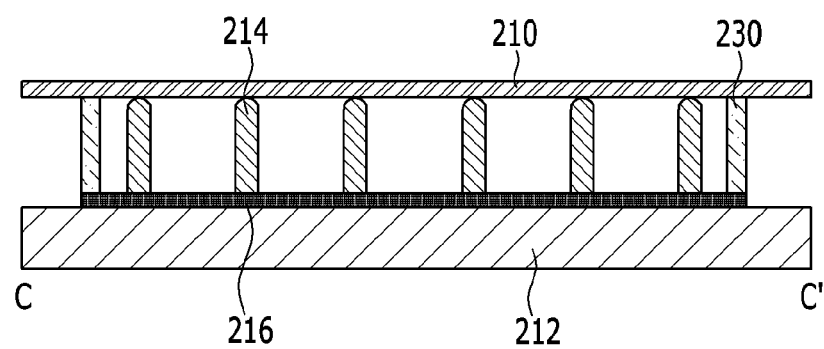
FIG. 8 is a cross-sectional view of the sensor unit taken along line C-C' of FIG. 6.

FIG. 6 is a perspective view illustrating a sensor unit 200 of the cochlear implant apparatus for active feedback control in accordance with a second exemplary embodiment of the present invention, FIG. 7 is a side view illustrating one side of the sensor unit 200 illustrated in FIG. 6, and FIG. 8 is a cross-sectional view of the sensor unit 200 taken along line C-C' of FIG. 6.

Referring to FIGS. 6 to 8, a plurality of actuators 230 disposed in the sensor unit 200 in accordance with the second exemplary embodiment of the present invention may be spaced apart from each other and may be spaced apart from each other and disposed in a plurality of base units 216, respectively.

In this case, each of the plurality of actuators 230 disposed in the respective base units 216 may be moved up and down in response to an electrical signal detected from the base unit 216 corresponding to each of the actuators 230.

In other words, each of the actuators 230 may be moved up and down in response to an electrical signal generated by the base unit 216 and nanopillars 214, disposed at a location corresponding to the location of the corresponding actuator 230, or in response to an electrical signal obtained by amplifying the generated electrical signal through the amplification unit 20.

Accordingly, the actuator 230 in accordance with the second exemplary embodiment of the present invention is advantageous in that it can control the selectivity of a sound for each frequency band.

Figure 9:
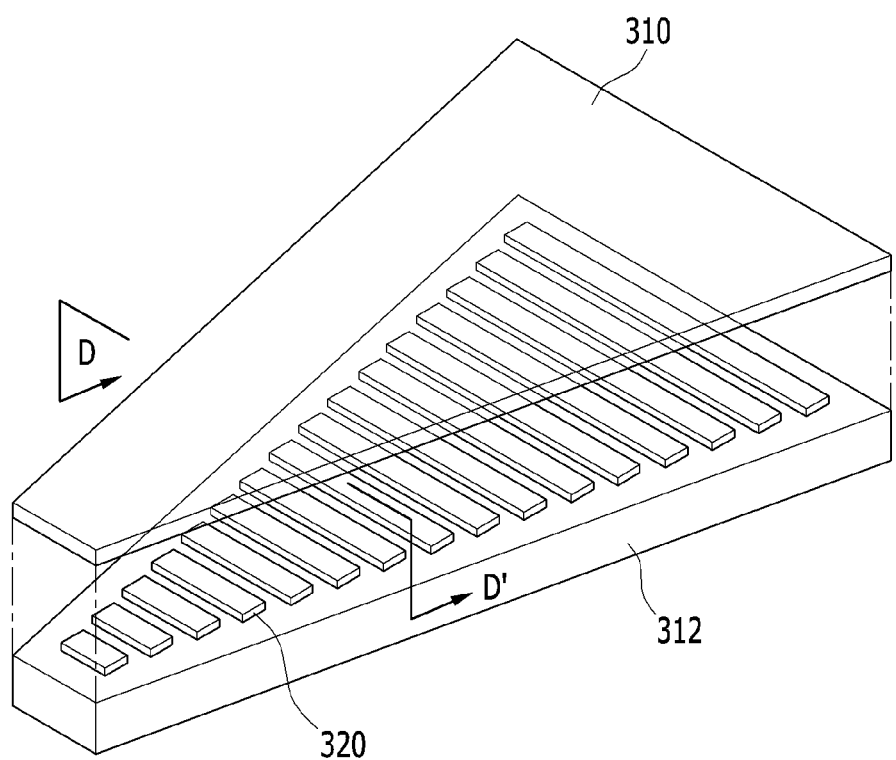
FIG. 9 is a perspective view of the sensor unit of the cochlear implant apparatus for active feedback control including a piezoelectric element in accordance with an exemplary embodiment of the present invention.
Figure 10:
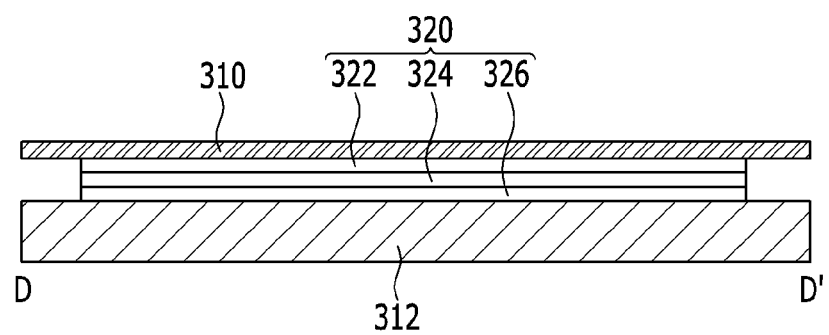
FIG. 10 is a cross-sectional view of the sensor unit taken along line D-D' of FIG. 9.

FIG. 9 is a perspective view of a sensor unit 300 of the cochlear implant apparatus for active feedback control including a piezoelectric element in accordance with an exemplary embodiment of the present invention, and FIG. 10 is a cross-sectional view of the sensor unit 300 taken along line D-D' of FIG. 9.

Referring to FIGS. 9 and 10, the sensor unit 300 of the cochlear implant apparatus for active feedback control equipped with the piezoelectric element according to an exemplary embodiment of the present invention includes a first substrate 310, a second substrate 312, and a frequency separation unit 320.

The first substrate 310 and the second substrate 312 are disposed to face each other so that they are symmetrical to each other. The frequency separation unit 320 is disposed between the first substrate 310 and the second substrate 312.

In this case the frequency separation units 320 is disposed between the first substrate 310 and the second substrate 312, and a plurality of the frequency separation units 320 is spaced apart from each other. Furthermore, each of the frequency separation units 320 includes a first electrode 322, a piezoelectric layer 324, and a second electrode 326.

The frequency separation unit 320 may have a structure in which the first electrode 322, the piezoelectric layer 324, and the second electrode 326 are sequentially stacked in a thickness direction from the top. That is, the frequency separation unit 320 includes the first electrode 322 and the second electrode 326 disposed to face each other and the piezoelectric layer 324 interposed between the first electrode 322 and the second electrode 326 and made of piezoelectric materials. The frequency separation unit 320 separates a sound according to each frequency band and generates an electrical signal.

At this time, the piezoelectric layer 324 that forms the frequency separation unit 320 detects the sound, vibrates, and generates a change of displacement. Each of the plurality of frequency separation units 320 has a unique resonant frequency in each region. When an acoustic wave is received, a random region of the piezoelectric layer 324 does not react and vibrate, but only a specific region of the piezoelectric layer 324 that has the frequency of the received acoustic wave as a resonant frequency reacts. Accordingly, the sensor unit 300 may detect vibration according to a sound in each frequency band through the frequency separation unit 320.

Figure 11:
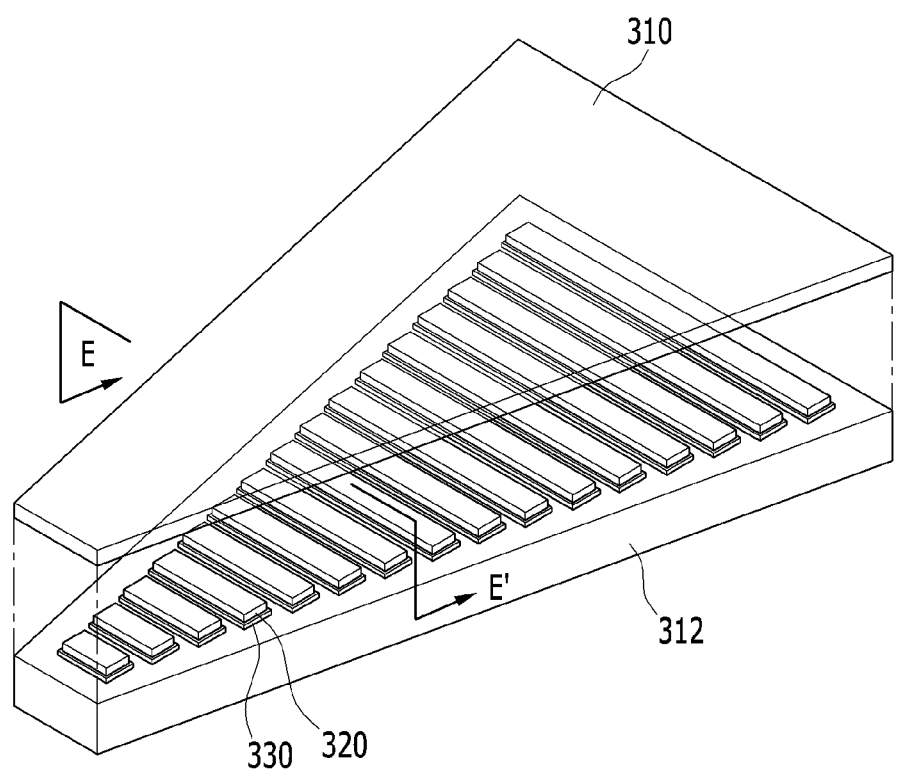
FIG. 11 is a perspective view illustrating a sensor unit of the cochlear implant apparatus for active feedback control in accordance with a third exemplary embodiment of the present invention.
Figure 12:
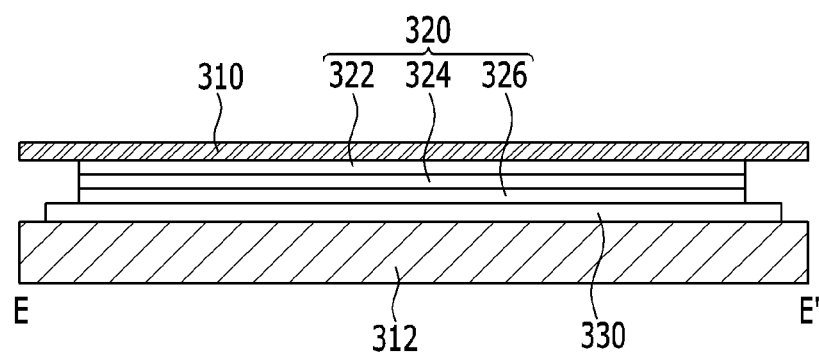
FIG. 12 is a cross-sectional view of the sensor unit taken along line E-E' of FIG. 11.
Figure 13:
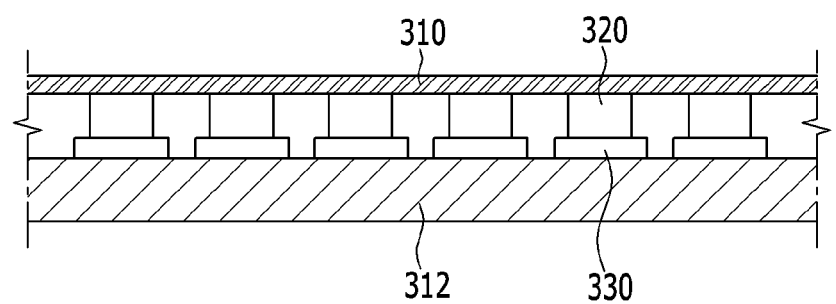
FIG. 13 is a side view illustrating one side of the sensor unit illustrated in FIG. 11.

FIG. 11 is a perspective view illustrating a sensor unit 300 of the cochlear implant apparatus for active feedback control in accordance with a third exemplary embodiment of the present invention, FIG. 12 is a cross-sectional view of the sensor unit 300 taken along line E-E' of FIG. 11, and FIG. 13 is a side view illustrating one side of the sensor unit 300 illustrated in FIG. 11.

Referring to FIGS. 11 to 13, a plurality of actuators 330 disposed in the sensor unit 300 in accordance with the third exemplary embodiment of the present invention is spaced apart from each other. The plurality of actuators 330 is disposed in respective frequency separation units 320.

In this case, the actuators 330 may be disposed in the plurality of respective frequency separation units 320, each configured to detect a sound in each frequency band, and may be disposed under the respective frequency separation units 320. In another embodiment, the actuator 330 may be disposed between a second electrode 326 and a piezoelectric layer 324.

Each of the actuators 330 may be deformed in response to an electrical signal according to a sound that is detected from the frequency separation unit 320 corresponding to the corresponding actuator 330.

In other words, each actuator 330 may be moved in response to an electrical signal generated by each frequency separation unit 320, disposed at a location corresponding to the location of the corresponding actuator 330, or in response to an electrical signal obtained by amplifying the generated electrical signal through the amplification unit 20.

Accordingly, the actuator 330 in accordance with the third exemplary embodiment of the present invention is advantageous in that it can control the selectivity of a sound according to each frequency band.

Figure 14:
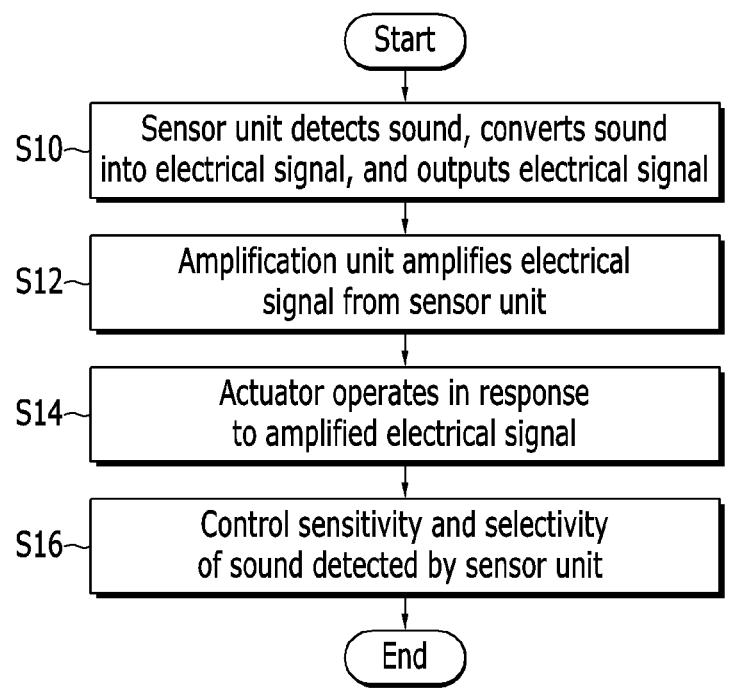
FIG. 14 is a flowchart illustrating a signal processing process of the cochlear implant apparatus for active feedback control in accordance with an exemplary embodiment of the present invention.

FIG. 14 is a flowchart illustrating a signal processing process of the cochlear implant apparatus for active feedback control in accordance with an exemplary embodiment of the present invention.

The method of controlling the sensitivity or selectivity of a sound in the sensor unit through the actuators in accordance with an exemplary embodiment of the present invention includes outputting an electrical signal, amplifying the signal, and driving the actuator.

In outputting an electrical signal, the sensor unit detects a sound within the human body, converts the detected sound into an electrical signal according to the magnitude of the detected sound, and outputs the converted electrical signal at step S10.

In amplifying the signal, the amplification unit receives the electrical signal from the sensor unit and amplifies the received electrical signal at step S12.

In driving the actuator, the actuator receives the amplified electrical signal from the amplifier and controls the sensitivity of the sound detected by the sensor unit or the selectivity of the sound in each frequency band in response to the electrical signal at step S14 and step S16.

While the configurations and operation of the cochlear implant apparatus for active feedback control have been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

<Description of reference numerals>

| | |
|---|---|
| 10, 100, 200, 300: sensor unit | 20: amplification unit |
| 30: control unit | 110, 210, 310: first substrate |
| 112, 212, 312: second substrate | 114, 214: nanopillar |
| 116, 216: based unit | 130, 230, 330: actuator |
| 320: frequency separation unit | 322: first electrode |
| 324: piezoelectric layer | 326: second electrode |

The invention claimed is:

1. A cochlear implant apparatus for active feedback control which is adapted to be located into a human body and configured to detect a sound in each of a plurality of frequency bands, the cochlear implant apparatus comprising:
a sensor unit configured to detect vibration according to a sound and generate an electrical signal corresponding to a magnitude of the vibration,
wherein the sensor unit comprises a first substrate, a second substrate disposed to face the first substrate, and actuators each of which is configured to receive and react to the generated electrical signal and to control sensitivity according to a magnitude of the sound or a selectivity of the sound detected in each of the plurality of frequency bands,
wherein each of the actuators extends in a direction perpendicular to the first substrate or the second substrate, and contacts the first substrate and the second substrate.

2. The cochlear implant apparatus of claim 1, further comprising:
an amplification unit configured to amplify the electrical signal from the sensor unit and provide the amplified electrical signal to the actuator; and
a control unit configured to process the amplified electrical signal received from the amplification unit and to provide the processed electrical signal to the amplification unit or the actuator.

3. The cochlear implant apparatus of claim 1, wherein the sensor unit comprises nanopillars or piezoelectric elements.

4. A cochlear implant apparatus for active feedback control, comprising a sensor unit,
the sensor unit comprising:
a first substrate;
a second substrate disposed to face the first substrate;
a plurality of base units disposed between the first substrate and the second substrate, the plurality of base units being configured to have different frequency bands and detects a sound in each of a plurality of frequency bands through the nanopillars formed in each of the plurality of base units; and
actuators provided separately from the plurality of base units between the first substrate and the second substrate and configured to support the first substrate and the second substrate and to react in response to an electrical signal,
wherein each of the actuators extends in a direction perpendicular to the first substrate or the second substrate and contacts the plurality of base units and the first substrate.

5. The cochlear implant apparatus of claim 4, wherein the actuators are disposed on both sides of the base units and are consecutively connected along the first substrate or the second substrate.

6. The cochlear implant apparatus of claim 4, wherein the electrical signal has been converted based on a magnitude of vibration corresponding to a sound detected by the sensor unit.

7. The cochlear implant apparatus of claim 4, wherein the actuators are disposed in the respective base units and spaced apart from each other.

8. The cochlear implant apparatus of claim 7, wherein each of the actuators disposed in the respective base units reacts in response to an electrical signal corresponding to a sound detected from each of the base units.

9. A cochlear implant apparatus for active feedback control, comprising a sensor unit, the sensor unit comprising:
a frequency separation unit comprising a first electrode, a second electrode disposed to face the first electrode, and piezoelectric layer made of piezoelectric material and interposed between the first electrode and the second electrode, the frequency separation unit separating the sound according to each of a plurality of frequency bands and generating an electrical signal; and
an actuator disposed to contact the frequency separation unit and configured to respond to the electrical signal and move the frequency separation unit.

10. The cochlear implant apparatus of claim 9, wherein the frequency separation unit is divided into a plurality of frequency separation units in order to detect a sound according to each of the plurality of frequency bands, and the actuator is disposed in each of the plurality of frequency separation units.

11. The cochlear implant apparatus of claim 9, wherein the actuator is disposed under the frequency separation unit.

12. An active feedback control method of a cochlear implant apparatus adapted to be located into a human body, comprising:

detecting, by a sensor unit, a sound, converting the detected sound into an electrical signal according to a magnitude of the detected sound, and outputting the converted electrical signal;

amplifying, by an amplification unit, the electrical signal received from the sensor unit; and receiving, by an actuator of the sensor unit, the amplified electrical signal from the amplification unit and controlling a sensitivity of the sound detected by the sensor unit or the selectivity of the sound in each frequency band in response to the electrical signal.

13. The method of claim 12, wherein the sensor unit comprises nanopillars or piezoelectric elements.

* * * * *